US009017945B2

(12) United States Patent
Smith

(10) Patent No.: US 9,017,945 B2
(45) Date of Patent: *Apr. 28, 2015

(54) METHOD FOR SEQUENCING A POLYNUCLEOTIDE TEMPLATE

(75) Inventor: Geoffrey Paul Smith, NR Saffron (GB)

(73) Assignee: Illumina Cambridge Limited, Nr Saffron Walden (GB)

(*) Notice: Subject to any disclaimer, the term of this patent is extended or adjusted under 35 U.S.C. 154(b) by 192 days.

This patent is subject to a terminal disclaimer.

(21) Appl. No.: 13/556,053

(22) Filed: Jul. 23, 2012

(65) Prior Publication Data

US 2013/0171648 A1    Jul. 4, 2013

Related U.S. Application Data

(63) Continuation of application No. 13/198,527, filed on Aug. 4, 2011, now Pat. No. 8,247,177, which is a continuation of application No. 11/989,172, filed as application No. PCT/GB2006/002690 on Jul. 20, 2006, now Pat. No. 8,017,335.

(30) Foreign Application Priority Data

Jul. 20, 2005  (GB) ................................ 0514910.9

(51) Int. Cl.
    *C12Q 1/68*    (2006.01)
(52) U.S. Cl.
    CPC ..................... *C12Q 1/6874* (2013.01)
(58) Field of Classification Search
    CPC .......................... C12Q 1/6874; C12Q 2535/119
    See application file for complete search history.

(56) References Cited

U.S. PATENT DOCUMENTS

| | | |
|---|---|---|
| 5,118,604 A | 6/1992 | Weissman et al. |
| 5,302,509 A | 4/1994 | Cheeseman |
| 5,547,839 A | 8/1996 | Dower et al. |
| 5,616,478 A | 4/1997 | Chetverin |
| 5,629,158 A | 5/1997 | Uhlen |
| 5,641,658 A | 6/1997 | Adams et al. |
| 5,800,992 A | 9/1998 | Fodor et al. |
| 5,837,466 A | 11/1998 | Lane et al. |
| 5,922,574 A | 7/1999 | Minter |
| 5,935,788 A | 8/1999 | Burmer et al. |

(Continued)

FOREIGN PATENT DOCUMENTS

| | | |
|---|---|---|
| DE | 10051564 | 8/2002 |
| EP | 0 224 126 | 6/1987 |

(Continued)

OTHER PUBLICATIONS

Adessi, et al., "Solid Phase DNA amplification: characterisation of primer attachment and amplification mechanisms", Nucleic Acids Research 28, 2000, 1-8.

(Continued)

*Primary Examiner* — Young J Kim
(74) *Attorney, Agent, or Firm* — Brent C. Moore; Illumina, Inc.

(57) ABSTRACT

The invention relates to methods for pairwise sequencing of a double-stranded polynucleotide template, which permit the sequential determination of nucleotide sequences in two distinct and separate regions on complementary strands of the double-stranded polynucleotide template. The two regions for sequence determination may or may not be complementary to each other.

17 Claims, 1 Drawing Sheet

(56) References Cited

U.S. PATENT DOCUMENTS

| | | | |
|---|---|---|---|
| 5,976,802 | A | 11/1999 | Ansorge et al. |
| 6,060,288 | A | 5/2000 | Adams et al. |
| 6,090,592 | A | 7/2000 | Adams et al. |
| 6,107,023 | A | 8/2000 | Reyes et al. |
| 6,251,610 | B1 | 6/2001 | Gupte et al. |
| 6,322,971 | B1 | 11/2001 | Chetverin et al. |
| 6,326,489 | B1 | 12/2001 | Church et al. |
| 6,361,947 | B1 | 3/2002 | Dong et al. |
| 6,511,803 | B1 | 1/2003 | Church et al. |
| 7,115,400 | B1 | 10/2006 | Adessi et al. |
| 7,754,429 | B2 | 7/2010 | Rigatti et al. |
| 8,017,335 | B2* | 9/2011 | Smith .................... 435/6.12 |
| 8,247,177 | B2* | 8/2012 | Smith .................... 435/6.11 |
| 2002/0055100 | A1 | 5/2002 | Kawashima et al. |
| 2002/0061532 | A1 | 5/2002 | Adams et al. |
| 2002/0081591 | A1 | 6/2002 | Lukhtanov et al. |
| 2002/0098499 | A1 | 7/2002 | Asp et al. |
| 2003/0022207 | A1 | 1/2003 | Balasubramanian et al. |
| 2003/0082576 | A1 | 5/2003 | Jones et al. |
| 2003/0108867 | A1 | 6/2003 | Chee |
| 2004/0002090 | A1 | 1/2004 | Mayer et al. |
| 2004/0096853 | A1 | 5/2004 | Mayer |
| 2004/0126765 | A1 | 7/2004 | Adams |
| 2005/0100900 | A1 | 5/2005 | Kawashima et al. |
| 2006/0024681 | A1 | 2/2006 | Smith et al. |
| 2006/0134633 | A1 | 6/2006 | Chen et al. |
| 2006/0292611 | A1 | 12/2006 | Berka et al. |
| 2007/0128624 | A1 | 6/2007 | Gormley et al. |
| 2008/0009420 | A1 | 1/2008 | Schroth et al. |
| 2009/0093378 | A1 | 4/2009 | Bignell et al. |

FOREIGN PATENT DOCUMENTS

| | | |
|---|---|---|
| EP | 0 356 021 | 2/1990 |
| EP | 0 374 665 | 6/1990 |
| EP | 0 438 292 | 7/1991 |
| EP | 0 201 184 | 12/1992 |
| EP | 0 534 858 | 3/1993 |
| EP | 0 665 293 | 8/1995 |
| EP | 0 763 135 | 3/1997 |
| EP | 1256632 | 11/2002 |
| EP | 1 591 541 | 11/2005 |
| EP | 1 647 602 | 4/2006 |
| EP | 2 032 686 | 3/2009 |
| GB | 0205153 | 4/2002 |
| GB | 2412170 | 9/2005 |
| GB | 0522310.2 | 12/2005 |
| WO | WO 89/01050 | 2/1989 |
| WO | WO 89/09282 | 10/1989 |
| WO | WO 92/10587 | 6/1992 |
| WO | WO 93/04199 | 3/1993 |
| WO | WO 94/02634 | 2/1994 |
| WO | WO 95/33073 | 12/1995 |
| WO | WO 96/04404 | 2/1996 |
| WO | WO 96/32504 | 10/1996 |
| WO | WO 98/36094 | 8/1998 |
| WO | WO 98/44151 | 10/1998 |
| WO | WO 98/44152 | 10/1998 |
| WO | WO 00/18957 | 4/2000 |
| WO | WO 00/75374 | 12/2000 |
| WO | WO 01/49882 | 7/2001 |
| WO | WO 01/79553 | 10/2001 |
| WO | WO 02/46456 | 6/2002 |
| WO | WO 03/056030 | 7/2003 |
| WO | WO 03/074734 | 9/2003 |
| WO | WO 2004/070005 | 8/2004 |
| WO | WO 2004/072294 | 8/2004 |
| WO | WO 2005/003375 | 1/2005 |
| WO | WO 2005/040425 | 5/2005 |
| WO | WO 2005/042781 | 5/2005 |
| WO | WO 2005/068656 | 7/2005 |
| WO | WO 2005/093094 | 10/2005 |
| WO | WO 2006/110855 | 10/2006 |
| WO | WO 2006/135342 | 12/2006 |
| WO | WO 2007/010251 | 1/2007 |
| WO | WO 2007/010252 | 1/2007 |
| WO | WO 2007/010263 | 1/2007 |
| WO | WO 2007/052006 | 5/2007 |
| WO | WO 2007/076726 | 7/2007 |
| WO | WO 2007/091077 | 8/2007 |
| WO | WO 2007/107710 | 9/2007 |
| WO | WO 2007/111937 | 10/2007 |
| WO | WO 2008/002502 | 1/2008 |

OTHER PUBLICATIONS

Bennett, et al., "Toward the $1000 Human Genome", Pharmacogenomics, Ashley Productions GB vol. 6 No. 4, 2005, 373-382.

Braslavsky, et al., "Sequence information can be obtained from single DNA molecules", PNAS, 100(7), 2003, 3960-3964.

Cheng, et al., "Chip PCR II Investigation of different PCR amplification systems in microfabricated silicon-glass chips", Nucleic Acids Research 24, 1996, 380-385.

Dubiley, et al., "Polymorphism analysis and gene detection by minisequencing on an array of gel-immobilized primers", Nucleic Acids Research 27, 1999, 1-6.

Frommer, et al., "A genomic sequencing protocol that yields a positive display of 5-methylcytosine residues in individual DNA strands", Proc Natl Acad Sci USA, 89 (5):1827-1831 (1992), 1992, 1827-1831.

Fu, et al., "Sequencing Double-stranded DNA by Strand Displacement", Nucleic Acids Research vol. 25 No. 3, 1997, 677-679.

Helfman, et al., "Identification of clones that encode chicken tropomyosin by direct immunological screening of a cDNA expression library", PNAS US 80, 1983, 31-35.

Kaderali, et al., Nucleic Acids Research, 31(6), 2003, 1796-1802.

Kalisch, et al., "Covalently linked sequencing primer linkers (splinkers) for sequence analysis of restriction fragments", Gene 44, 1986, 263-270.

Kimmel, et al., "Preparation of cDNA and the Generation of cDNA Libraries: Overview", Methods in Enzymology 152, 1987, 307-316.

Kinzler, et al., "Whole genome PCR: application to the identification of sequences bound by gene regulatory proteins", Nucleic Acids Research, 17(10), 1989, 3645-3653.

Lucito, et al., "Genetic analysis using genomic representations", PNAS, 95, 1998, 4487-4492.

Mardis, "Next-generation DNA sequencing methods", Annual Review of Genomics and Human Genetics, Sep. 2008, 387-402.

Margulies, Marcel et al., "Genome Sequencing in microfabricated high-density picolitre reactors", Nature, vol. 437 No. 7057, Jul. 31, 2005, 376-380.

Matsunaga, et al., "Selecting and amplifying one fragment from a DNA fragment mixture by polyermerase chain reaction with a pair of selective primers", Electrophoresis, vol. 17, 1996, 1833-1840.

Ng, et al., "Multiplex sequencing of paired-end ditags (MS-PET): a strategy for the ultra-high-throughput analysis of transcriptomes and genomes", Nucleic Acids research 2006—vol. 34 No. 12, Jul. 2006, E84.

O'Meara, et al., "SNP typing by apyrase-mediated allele-specific primer extension on DNA microarrays", NAR, 30, 2002, 1-8.

Oroskar, et al., "Detection of immobilized amplicons by ELISA-like techniques", Clinical Chemistry 42, 1996, 1547-1555.

Roach, et al., "Pairwise end sequencing: A unified approach to genomic mapping and sequencing", Genomics 26, 1995, 345-353.

Saiki, et al., "Analysis of enzymatically amplified . . . -globin and HLA-DQ . . . DNA with allele-specific oligonucleotide probes", Nature 324, 1986, 163-166.

Saiki, et al., "Primer-Directed Enzymatic Amplification of DNA with a Thermostable DNA Polymerase", Science 239, 1988, 487-491.

San Luis, et al., "Analysis of a gene (vch) encoding hemolysin isolated and sequenced from *Vibrio campbellii*", Journal of general and Applied Microbiology; vol. 52; No. 6, Dec. 2006, 303-313.

(56) References Cited

OTHER PUBLICATIONS

Sanger, et al., "Cloning in Single-Stranded Bacteriophage as an Aid to Rapid DNA Sequencing", Mol Biologiy 143, 1980, 161-178.

Sarkar, et al., "Restriction-site PCR: A direct method of unknown sequence retrieval adjacent to a known locus by using universal primers", PCR Methods and Applications, 1993, 2:318-322.

Shapero, et al., "SNP Genotyping by multiplexed solid-phase amplification and fluorescent minisequencing", Genome Research vol. 11 No. 11, 2001, 1926-1934.

Shendure, et al., "Accurate Multiplex Polony Sequencing of an Evolved Bacterial Genome", Science, vol. 309, vol. 309 No. 5741, 2005, 1728-1732.

Shi, "Enablling large-scale Pharmacogenetic studies by high-throughput mutation detection and genotyping technologies", Clinical Chemistry vol. 47 No. 2, 2000, 164-172.

Solexa, "Solexa Application Note: DNA Sequencing", 2006.

Sterky, et al., "Direct sequencing of bacterial artificial chromosomes [bacS] prokaryotic genomes by biotin capture PCR", Journal of Biotechnology, vol. 60, 1998, 119-129.

Strick, et al., "Stress-Induced Structural Transistions of DNA and Proteins", Annu Rev. Biophys. Biomol. Struct. 29, 2000, 523-543.

Velculescu, et al., "Serial analysis of gene expression", Science, 270, 1995, 484-487.

Warren, Rene et al., "Assembling Millions of short DNA sequences using SSAKE", Bioinformatics (Oxford) vol. 23 No. 4, 2007, 500-501.

Westin, et al., "Anchored multiplex amplification on a microelectric chip array", Nature Biotechnology 18, 2000, 199-204.

Wiemann, et al., "Doublex Fluorescent DNA sequencing: two independent sequences obtained simultaneously in one reaction with internal labeling and unlabeled primers", Analytical Biochemistry US, 1996, 166-174.

\* cited by examiner

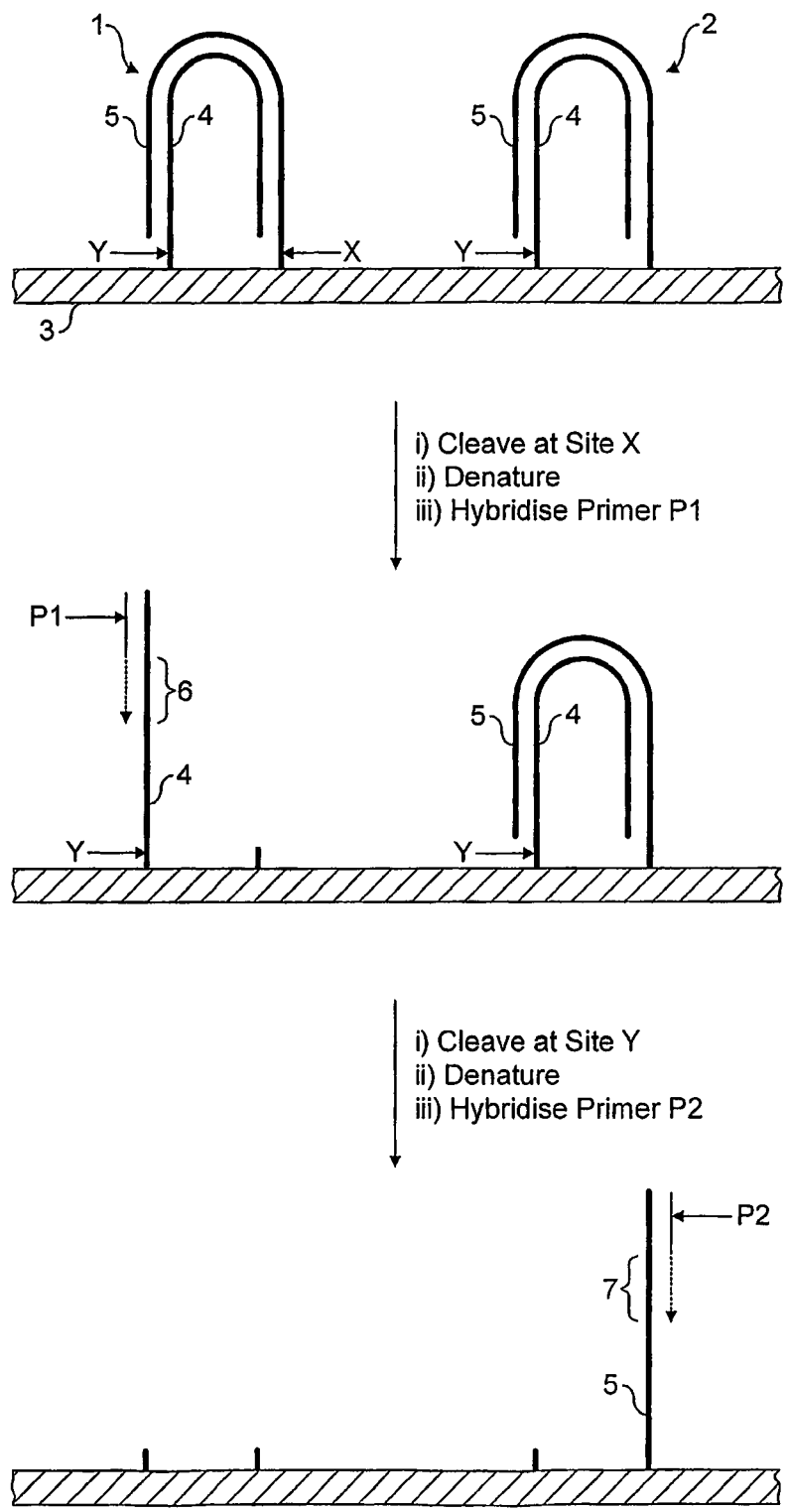

METHOD FOR SEQUENCING A POLYNUCLEOTIDE TEMPLATE

CROSS-REFERENCE TO RELATED APPLICATIONS

This application is a continuation application of U.S. application Ser. No. 13/198,527, filed Aug. 4, 2011, now U.S. Pat. No. 8,247,177, which is a continuation application of U.S. application Ser. No. 11/989,172, filed Feb. 24, 2009, now U.S. Pat. No. 8,017,335, which is a National Stage Application of International Application No. PCT/GB2006/002690, filed Jul. 20, 2006, which claims the priority of Great Britain Application No. GB 0514910.9, filed Jul. 20, 2005. The contents of all these applications are hereby incorporated by reference in their entireties.

FIELD OF THE INVENTION

The invention relates to methods for pairwise sequencing of a double-stranded polynucleotide template, which methods result in the sequential determination of nucleotide sequences in two distinct and separate regions of the polynucleotide template.

BACKGROUND TO THE INVENTION

Advances in the study of biological molecules have been led, in part, by improvement in technologies used to characterise the molecules or their biological reactions. In particular, the study of the nucleic acids DNA and RNA has benefited from developing technologies used for sequence analysis.

U.S. Pat. No. 5,302,509 describes a method for sequencing a polynucleotide template which involves performing multiple extension reactions using a DNA polymerase or DNA ligase to successively incorporate labelled polynucleotides complementary to a template strand. In such a "sequencing by synthesis" reaction a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

In order to carry out accurate sequencing a reversible chain-terminating structural modification or "blocking group" may be added to the substrate nucleosides to ensure that nucleotides are incorporated one at a time in a controlled manner. As each single nucleotide is incorporated, the blocking group prevents any further nucleotide incorporation into the polynucleotide chain. Once the identity of the last-incorporated labelled nucleotide has been determined the label moiety and blocking group are removed, allowing the next blocked, labelled nucleotide to be incorporated in a subsequent round of sequencing.

In certain circumstances the amount of sequence data that can be reliably obtained with the use of sequencing-by-synthesis techniques, particularly when using blocked, labelled nucleotides, may be limited. In some circumstances it is preferred to limit the sequencing "run" to a number of bases that permits sequence realignment with the human genome, typically around 25-30 cycles of incorporation. Whilst sequencing runs of this length are extremely useful, particularly in applications such as, for example, SNP analysis and genotyping, it would be advantageous in many circumstances to be able to reliably obtain further sequence data for the same template molecule.

The technique of "paired-end" or "pairwise" sequencing is generally known in the art of molecular biology, particularly in the context of whole-genomic shotgun sequencing (Siegel A. F. et al., Genomics. 2000, 68: 237-246; Roach J. C. et al., Genomics. 1995, 26: 345-353). Paired-end sequencing allows the determination of two "reads" of sequence from two places on a single polynucleotide template. The advantage of the paired-end approach is that there is significantly more information to be gained from sequencing two stretches each of "n" bases from a single template than from sequencing "n" bases from each of two independent templates in a random fashion. With the use of appropriate software tools for the assembly of sequence information (Millikin S. C. et al., Genome Res. 2003, 13: 81-90; Kent, W. J. et al., Genome Res. 2001, 11: 1541-8) it is possible to make use of the knowledge that the "paired-end" sequences are not completely random, but are known to occur on a single template, and are therefore linked or paired in the genome. This information has been shown to greatly aid the assembly of whole genome sequences into a consensus sequence.

Paired-end sequencing has typically been performed by making use of specialized circular shotgun cloning vectors known in the art. After cutting the vector at a specific single site, the template DNA to be sequenced (typically genomic DNA) is inserted into the vector and the ends resealed to form a new construct. The vector sequences flanking the insert DNA include binding sites for sequencing primers which permit sequencing of the insert DNA on opposite strands.

A disadvantage of this approach is that it requires time-consuming cloning of the DNA templates it is desired to sequence into an appropriate sequencing vector. Furthermore, because of the need to clone the DNA template into a vector in order to position binding sites for sequencing primers at both ends of the template fragment it is extremely difficult to make use of array-based sequencing techniques. With array-based techniques it is generally only possible to sequence from one end of a nucleotide template, this often being the end proximal to the point of attachment to the array.

WO 2004/070005 describes a method for double-ended sequencing of a polynucleotide template which can be carried out on a solid support. The method relies on simultaneous hybridisation of two or more primers to a target polynucleotide in a single primer hybridization step. Following the hybridization step, all of the primers hybridized to the template are blocked except for one, which has a free 3' hydroxyl group which serves as an initiation point for a first sequencing reaction. Sequencing proceeds until no further chain elongation is possible, or else the sequencing reaction is terminated. Then one of the blocked primers is unblocked to give a free 3' hydroxyl and a second sequencing reaction is performed from this initiation point. Thus, the template remains intact and attached to the solid support throughout.

A major drawback of this approach based in hybridisation of blocked and unblocked primers is that if it is desired to sequence two regions on complementary strands of a double-stranded nucleic acid template then it is necessary to hybridise primers to both complementary strands of the template in a single hybridisation step. Since both strands of the template remain intact and attached to the solid support, hybridisation of the primers to cognate sequences in the template strands will generally be unfavourable, against formation of a duplex by annealing of the two complementary strands of the template.

WO 98/44151 and WO 00/18957 both describe methods of nucleic acid amplification which allow amplification products to be immobilised on a solid support in order to form arrays comprised of clusters or "colonies" formed from a plurality of identical immobilised polynucleotide strands and a plurality of identical immobilised complementary strands. The nucleic acid molecules present in DNA colonies on the clustered arrays prepared according to these methods can provide templates for sequencing reactions, for example as described in WO 98/44152, but to date only a single sequencing read can be obtained from one type of immobilised strand in each colony.

The present inventors have now developed a method for paired-end sequencing of double-stranded polynucleotide templates, including double-stranded templates present on clustered arrays, such as those described in WO 98/44151 and WO 00/18957. The method permits sequencing of two distinct regions on complementary strands of a target polynucleotide duplex and is based on controlled formation of single-stranded templates which permit hybridisation of a sequencing primer. Using the method of the invention it is possible to obtain two linked or paired reads of sequence information from each double-stranded template on a clustered array, rather than just a single sequencing read as can be obtained with prior art methods.

SUMMARY OF THE INVENTION

According to the invention there is provided a method for pairwise sequencing of first and second regions of a target double-stranded polynucleotide, wherein said first and second regions are in complementary strands of the target polynucleotide, the method comprising:
(a) providing a solid support having immobilised thereon a plurality of template polynucleotide duplexes each comprising a double-stranded target polynucleotide, wherein each template duplex is formed from complementary first and second template strands linked to the solid support at their 5' ends;
(b) cleaving the second template strands of a sub-fraction of the template polynucleotide duplexes to remove all or a portion of said strands, thereby generating single-stranded regions on the complementary first template strands;
(c) hybridising first sequencing primers to the single-stranded regions of the first template strands generated in part (b);
(d) carrying out a first sequencing reaction by sequential addition of nucleotides to the first sequencing primer to determine the sequence of a first region of the target polynucleotide in the first template strand;
(e) cleaving the first template strands of substantially all the template polynucleotide duplexes to remove all or a portion of said strands, thereby generating single-stranded regions on the second template strands that were not cleaved in step (b);
(f) hybridising a second sequencing primer to the single-stranded regions of the second template strands generated in part (e); and
(g) carrying out a second sequencing reaction by sequential addition of nucleotides to the second sequencing primer to determine the sequence of a second region of the target polynucleotide in the second template strand.

Cleavage steps (b) and (e) may involve cleavage at predetermined cleavage sites in the respective template strands.

In one embodiment the "plurality" of template duplexes provided in step (a) may comprise a mixture of first and second template duplexes, wherein only the first duplexes are capable of being cleaved in the first cleavage reaction of step (b), but both first and second duplexes can be cleaved in the second cleavage reaction of step (e).

In one embodiment, the plurality of template duplexes provided in step (a) are formed within a single cluster or "colony" from a single originating template or target polynucleotide sequence by solid-phase PCR amplification, wherein a fraction of the duplexes within such cluster or colony (referred to herein as first template duplexes) are capable of being cleaved in the first cleavage reaction of step (b), and other duplexes within the same cluster or colony (referred to herein as second template duplexes) are not capable of cleavage in the first cleavage reaction of step (b), and both first and second template duplexes are capable of being cleaved in the second cleavage reaction of step (e).

In a particular embodiment, the cluster or colony comprising the first and second template duplexes itself forms part of an array of such clusters or colonies formed by solid-phase PCR amplification. Each individual cluster on such a clustered array may be derived from a different template or target molecule and the array as a whole may be prepared by solid-phase PCR amplification of a library of different template or target molecules. Preferably each single template molecule within the library of template molecules gives rise to a separate cluster or colony on the array comprising only first and second template duplexes derived from that single template molecule.

In a non-limiting embodiment the invention provides a method for pairwise sequencing of first and second regions of a target double-stranded polynucleotide, wherein said first and second regions are in complementary strands of the target polynucleotide, the method comprising the steps of:
(a) providing a solid support having immobilised thereon a mixture of first and second template polynucleotide duplexes each comprising the same double-stranded target polynucleotide, wherein both strands of each template polynucleotide duplex are linked to the solid support at the 5' end, a first template strand of both the first and second template polynucleotide duplexes includes a cleavage site Y and a second template strand of the first template polynucleotide duplexes but not the second template polynucleotide duplexes includes a cleavage site X, which is different to cleavage site Y;
(b) cleaving a second template strand of the first template polynucleotide duplexes at cleavage site X;
(c) hybridising a first sequencing primer to the first template strand of the first template polynucleotide duplexes;
(d) carrying out a first sequencing reaction by sequential addition of nucleotides to the first sequencing primer to determine the sequence of a first region of the target polynucleotide in the first template strand;
(e) cleaving a first template strand of both the first and second template polynucleotide duplexes at cleavage site Y,
(f) hybridising a second sequencing primer to the second template strand of the second template polynucleotide duplexes; and
(g) carrying out a second sequencing reaction by sequential addition of nucleotides to the second sequencing primer to determine the sequence of a second region of the target polynucleotide in the second template strand.

BRIEF DESCRIPTION OF THE DRAWINGS

FIG. 1. is a schematic illustration of an embodiment of the method of the invention. For simplicity, only two template duplexes are shown.

DETAILED DESCRIPTION OF THE INVENTION

The invention provides a method for sequencing two regions of a target double-stranded polynucleotide template, referred to herein as the first and second regions for sequence determination. The first and second regions for sequence determination are on complementary strands of the double-stranded polynucleotide template, which are referred to herein respectively as first and second template strands. The two regions for sequence determination may or may not be complementary to each other.

In order to sequence two regions on complementary strands of a given target double-stranded polynucleotide using the method of the invention it is necessary to carry out separate sequencing reactions on the two complementary strands. To enable two separate sequencing reactions it is in turn necessary to sequentially form single-stranded regions in each of the two complementary strands which can serve as templates for sequencing, allowing hybridisation of suitable sequencing primers for a sequencing reaction. Formation of suitable single-stranded regions for sequencing on complementary strands of a double-stranded template is achieved in the method of the invention by sequential controlled cleavage of the two strands of the double-stranded polynucleotide. Each cleavage step results in removal of at least a portion of one strand of a double-stranded molecule, leaving behind a single-stranded region on the complementary (uncleaved) strand. A conventional sequencing primer may then be hybridised to the single-stranded region.

The cleavage steps may involve chemical, enzymatic or photochemical cleavage, as discussed in further detail below.

The starting point for the method of the invention is the provision of a plurality of template polynucleotide duplexes immobilised on a solid support. Each of the duplexes comprises the same double-stranded target region to be sequenced. The duplexes are each formed from complementary first and second template strands which are linked to the solid support at or near to their 5' ends. Typically, the template polynucleotide duplexes will be provided in the form of a clustered array.

When referring to immobilisation or attachment of molecules (e.g. nucleic acids) to a solid support, the terms "immobilised" and "attached" are used interchangeably herein and both terms, are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc) which has been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

The first step of the method involves cleavage of one strand of the template duplex to generate a suitable template for a first sequencing reaction. This first cleavage step results in the removal of all or a portion of one strand of the polynucleotide duplex (denoted the second template strand) from the solid support. Cleavage of all or part of the second template strand leaves behind a single-stranded region on the complementary strand of the duplex (denoted the first template strand since it will be sequenced in the first sequencing reaction) still attached to the support. A first sequencing reaction may then be carried out by hybridising a suitable sequencing primer to the single-stranded region.

It is essential that only a sub-fraction of the whole plurality of template duplexes immobilised on the support are cleaved in this first cleavage step, such that a sufficient intact duplexes comprising "uncleaved" second template strands are left on the support to form templates for a second sequencing reaction. The sub-fraction of duplexes cleaved in the first cleavage step will preferably be close to half.

When the first sequencing reaction is complete a second cleavage step is carried out on the "intact" duplexes remaining on the solid support in order to generate suitable templates for sequencing a region of the second template strand. This second cleavage step results in removal of all or a portion of at least the first template strands which are present in "intact" template duplexes remaining on the solid support and may remove all first template strands attached to the support (including those paired with "cleaved" second strands). Provided that at least the first strands in intact duplexes are cleaved, this second cleavage will leave behind single-stranded regions on the remainder of the second template strands that were not cleaved in the first cleavage step. A second sequencing reaction may then be carried out by hybridising a suitable sequencing primer to the single-stranded region.

As discussed above, a key feature of the method of the invention is that sequential cleavage of the template duplexes is controlled, such that only a sub-fraction of the total duplexes immobilised on the support are cleaved in the first cleavage step, leaving a significant number of intact duplexes to be cleaved in the second cleavage step. In one non-limiting embodiment this may be achieved by providing as a starting material a mixture of first and second polynucleotide template duplexes immobilised on the solid support. The first and second polynucleotide template duplexes will each comprise the same (or substantially the same) target double-stranded polynucleotide, but the first and second duplexes also have different features which permit controlled sequential cleavage.

The first and second duplexes are each comprised of complementary first and second template nucleic acid strands. The first template strand of both the first and the second template duplexes includes a cleavage site Y. Cleavage site Y is a site which allows controlled cleavage of the first template strand by chemical, enzymatic or photochemical means. Cleavage at site Y results in removal of a portion of the first template strand, leaving behind a single-stranded region on the complementary second template strand. A sequencing primer can then be hybridised to the single-stranded region.

The second template strand of the first template polynucleotide duplexes, but not the second template polynucleotide duplexes, includes a cleavage site X. Thus, the first and second duplexes differ due to the presence or absence of cleavage site X. Cleavage site X is a site which allows controlled cleavage of the second template strand by chemical, enzymatic or photochemical means. Cleavage at site X results in removal of a portion of the second template strand, leaving behind a single-stranded region on the complementary first template strand. A sequencing primer can then be hybridised to the single-stranded region.

It is essential for performance of this embodiment of the method that cleavage sites X and Y are different, so that the first and second template strands can be independently cleaved. More specifically, it is essential that any external agent (e.g. chemical agent or restriction enzyme) used to cleave at site X, where present in the second template strands, does not also cleave the first template strands at site Y.

Any suitable enzymatic, chemical or photochemical cleavage reaction may be used to cleave at site X or site Y. The cleavage reaction may result in removal or a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulphide linkage with a reducing agent (e.g. TCEP), in which case the cleavage site should include an appropriate disulphide linkage; chemical cleavage of a diol linkage with periodate, in which case the cleavage site should include a diol linkage; generation of an abasic site and subsequent hydrolysis, etc.

In one embodiment cleavage may occur at a cleavage site in one or both strands of a template polynucleotide duplex which comprises one or more or any combination of non-natural nucleotides, ribonucleotides or a non-nucleotide chemical modifications.

Suitable cleavage techniques for use in the method of the invention include, but are not limited to, the following:
i) Chemical Cleavage The term "chemical cleavage" encompasses any method which utilises a non-nucleic acid and non-enzymatic chemical reagent in order to promote/achieve cleavage of one or both strands of a template polynucleotide duplex. If required, one or both strands of the template polynucleotide duplex may include one or more non-nucleotide chemical moieties and/or non-natural nucleotides and/or non-natural backbone linkages in order to permit chemical cleavage reaction. In a preferred embodiment the modification(s) required to permit chemical cleavage may be incorporated into an amplification primer used to form the template polynucleotide duplex by solid-phase nucleic acid amplification.

In a preferred but non-limiting embodiment one strand of the template polynucleotide duplex (or the amplification primer from which this strand is derived if formed by solid-phase amplification) may include a diol linkage which permits cleavage by treatment with periodate (e.g. sodium periodate). It will be appreciate that more than one diol can be included at the cleavage site.

Diol linker units based on phosphoamidite chemistry suitable for incorporation into polynucleotide chains are commercially available from Fidelity systems Inc. (Gaithersburg, Md., USA). One or more diol units may be incorporated into a polynucleotide using standard methods for automated chemical DNA synthesis. Hence, oligonucleotide primers including one or more diol linkers can be conveniently prepared by chemical synthesis.

In order to position the diol linker at an optimum distance from the solid support one or more spacer molecules may be included between the diol linker and the site of attachment to the solid support. The spacer molecule may be a non-nucleotide chemical moiety. Suitable spacer units based on phosphoamidite chemistry for use in conjunction with diol linkers are also supplied by Fidelity Systems Inc. One suitable spacer for use with diol linkers is the spacer denoted arm 26, identified in the accompanying examples. To enable attachment to a solid support at the 5' end of the polynucleotide strand arm 26 may be modified to include a phosphorothioate group. The phosphorothioate group can easily be attached during chemical synthesis of a "polynucleotide" chain including the spacer and diol units.

Other spacer molecules could be used as an alternative to arm 26. For example, a stretch of non-target "spacer" nucleotides may be included. Typically from 1 to 20, more preferably from 1 to 15 or from 1 to 10, and more particularly 2, 3, 4, 5, 6, 7, 8, 9 or 10 spacer nucleotides may be included. Most preferably 10 spacer nucleotides will be positioned between the point of attachment to the solid support and the diol linker. It is preferred to use polyT spacers, although other nucleotides and combinations thereof can be used. In one preferred embodiment 10T spacer nucleotides may be used.

The diol linker is cleaved by treatment with a "cleaving agent", which can be any substance which promotes cleavage of the diol. The preferred cleaving agent is periodate, preferably aqueous sodium periodate ($NaIO_4$). Following treatment with the cleaving agent (e.g. periodate) to cleave the diol, the cleaved product may be treated with a "capping agent" in order to neutralise reactive species generated in the cleavage reaction. Suitable capping agents for this purpose include amines, such as ethanolamine. Advantageously, the capping agent (e.g. ethanolamine) may be included in a mixture with the cleaving agent (e.g. periodate) so that reactive species are capped as soon as they are formed.

The combination of a diol linkage and cleaving agent (e.g. periodate) to achieve cleavage of one strand of a template polynucleotide duplex is preferred for linearisation of template duplexes on solid supported polyacrylamide hydrogels because treatment with periodate is compatible with nucleic acid integrity and with the chemistry of the hydrogel surface. However, utility of diol linkages/periodate as a method of linearisation is not limited to polyacrylamide hydrogel surfaces but also extends to linearisation of duplexes immobilised on other solid supports and surfaces, including supports coated with functionalised silanes (etc).

In a further embodiment, the strand to be cleaved (or the amplification primer from which this strand is derived if prepared by solid-phase amplification) may include a disulphide group which permits cleavage with a chemical reducing agent, e.g. Tris(2-carboxyethyl)-phosphate hydrochloride (TCEP).

ii) Cleavage of Abasic Sites

An "abasic site" is defined as a nucleoside position in a polynucleotide chain from which the base component has been removed. Abasic sites can occur naturally in DNA under physiological conditions by hydrolysis of nucleoside residues, but may also be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a polynucleotide strand.

In a preferred but non-limiting embodiment an abasic site may be created at a pre-determined position on one strand of a template polynucleotide duplex and then cleaved by first incorporating deoxyuridine (U) at a pre-determined cleavage site in one strand of the template polynucleotide duplex. This can be achieved, for example, by including U in one of the primers used for preparation of the template polynucleotide duplex by solid-phase PCR amplification. The enzyme uracil DNA glycosylase (UDG) may then be used to remove the uracil base, generating an abasic site on one strand. The polynucleotide strand including the abasic site may then be cleaved at the abasic site by treatment with endonuclease (e.g.

EndoIV endonuclease, AP lyase, FPG glycosylase/AP lyase, EndoVIII glycosylase/AP lyase), heat or alkali.

Abasic sites may also be generated at non-natural/modified deoxyribonucleotides other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV, AP lyase). If the non-natural/modified nucleotide is to be incorporated into an amplification primer for use in solid-phase amplification, then the non-natural/modified nucleotide should be capable of being copied by the polymerase used for the amplification reaction.

In one embodiment, the molecules to be cleaved may be exposed to a mixture containing the appropriate glycosylase and one or more suitable endonucleases. In such mixtures the glycosylase and the endonuclease will typically be present in an activity ratio of at least about 2:1.

This method of cleavage has particular advantages in relation to the creation of templates for nucleic acid sequencing. In particular, cleavage at an abasic site generated by treatment with a glycosylase such as UDG generates a free 3' hydroxyl group on the cleaved strand which can provide an initiation point for sequencing a region of the complementary strand. Moreover, if the starting double-stranded nucleic acid contains only one cleavable (e.g. uracil) base on one strand then a single "nick" can be generated at a unique position in this strand of the duplex. Since the cleavage reaction requires a residue, e.g. deoxyuridine, which does not occur naturally in DNA, but is otherwise independent of sequence context, if only one non-natural base is included there is no possibility of glycosylase-mediated cleavage occurring elsewhere at unwanted positions in the duplex. In contrast, were the double-stranded nucleic acid to be cleaved with a "nicking" endonuclease that recognises a specific sequence, there is a possibility that the enzyme may create nicks at "other" sites in the duplex (in addition to the desired cleavage site) if these possess the correct recognition sequence. This could present a problem if nicks are created in the strand it is intended to sequence rather than the strand that will be fully or partially removed to create the sequencing template and is a particular risk if the target portion of the double-stranded nucleic acid molecule is of unknown sequence.

The fact that there is no requirement for the non-natural (e.g. uracil) residue to be located in a detailed sequence context in order to provide a site for cleavage using this approach is itself advantageous. In particular, if the cleavage site is to be incorporated into an amplification primer to be used in the production of a clustered array by solid-phase amplification, it is necessarily only to replace one natural nucleotide (e.g. T) in the primer with a non-natural nucleotide (e.g. U) in order to enable cleavage. There is no need to engineer the primer to include a restriction enzyme recognition sequence of several nucleotides in length. Oligonucleotide primers including U nucleotides, and the other non-natural nucleotides listed above, can easily be prepared using conventional techniques and apparatus for chemical synthesis of oligonucleotides.

Another advantage gained by cleavage of abasic sites in a double-stranded molecule generated by action of UDG on uracil is that the first base incorporated in a "sequencing-by-synthesis" reaction initiating at the free 3' hydroxyl group formed by cleavage at such a site will always be T. Hence, if the template polynucleotide duplex forms part of a clustered array comprised of many such molecules, all of which are cleaved in this manner to produce sequencing templates, then the first base universally incorporated across the whole array will be T. This can provide a sequence-independent assay for cluster intensity at the start of a sequencing "run".

iii) Cleavage of Ribonucleotides

Incorporation of one or more ribonucleotides into a polynucleotide strand which is otherwise comprised of deoxyribonucleotides (with or without additional non-nucleotide chemical moieties, non-natural bases or non-natural backbone linkages) can provide a site for cleavage using a chemical agent capable of selectively cleaving the phosphodiester bond between a deoxyribonucleotide and a ribonucleotide or using a ribonuclease (RNAse). Therefore, sequencing templates can be produced by cleavage of one strand of a template polynucleotide duplex at a site containing one or more consecutive ribonucleotides using such a chemical cleavage agent or an RNase. Preferably the strand to be cleaved contains a single ribonucleotide to provide a site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g. treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimise chemical (or enzymatic) cleavage. By way of example, rUMP or rCMP are generally preferred if cleavage is to be carried out by exposure to metal ions, especially rare earth metal ions.

The ribonucleotide(s) will typically be incorporated into one strand of a template polynucleotide duplex (or the amplification primer from which this strand is derived if prepared by solid-phase amplification), and may be situated in a region of the duplex which is single-stranded when the two complementary strands of the duplex are annealed (i.e. in a 5' overhanging portion). If the template polynucleotide duplex is prepared by solid-phase PCR amplification using forward and reverse amplification primers, one of which contains at least one ribonucleotide, the standard DNA polymerase enzymes used for PCR amplification are not capable of copying ribonucleotide templates. Hence, the PCR products will contain an overhanging 5' region comprising the ribonucleotide(s) and any remainder of the amplification primer upstream of the ribonucleotide(s).

The phosphodiester bond between a ribonucleotide and a deoxyribonucleotide, or between two ribonucleotides may also be cleaved by an RNase. Any endocytic ribonuclease of appropriate substrate specificity can be used for this purpose. If the ribonucleotide(s) are present in a region which is single-stranded when the two complementary strands of the double-stranded molecule are annealed (i.e. in a 5' overhanging portion), then the RNase will be an endonuclease which has specificity for single strands containing ribonucleotides. For cleavage with ribonuclease it is preferred to include two or more consecutive ribonucleotides, and preferably from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Polynucleotides incorporating one or more ribonucleotides can be readily synthesised using standard techniques for oligonucleotide chemical synthesis with appropriate ribonucleotide precursors. If the template polynucleotide duplex is prepared by solid-phase nucleic acid amplification, then it is convenient to incorporate one or more ribonucleotides into one of the primers to be used for the amplification reaction.

iv) Photochemical Cleavage

The term "photochemical cleavage" encompasses any method which utilises light energy in order to achieve cleavage of one or both strands of the double-stranded nucleic acid molecule.

A site for photochemical cleavage can be provided by a non-nucleotide chemical spacer unit in one of the strands of the double-stranded molecule (or the amplification primer from which this strand is derived if prepared by solid-phase amplification). Suitable photochemical cleavable spacers include the PC spacer phosphoamidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

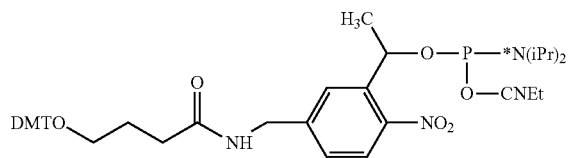

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable template polynucleotide duplex by solid-phase amplification.

v) Cleavage of Hemimethylated DNA

Site-specific cleavage of one strand of a double-stranded nucleic acid molecule may also be achieved by incorporating one or more methylated nucleotides into this strand and then cleaving with an endonuclease enzyme specific for a recognition sequence including the methylated nucleotide(s).

The methylated nucleotide(s) will typically be incorporated in a region of one strand of the template polynucleotide duplex having a complementary stretch of non-methylated deoxyribonucleotides on the complementary strand, such that annealing of the two strands produces a hemimethylated duplex structure. The hemimethylated duplex may then be cleaved by the action of a suitable endonuclease. For the avoidance of doubt, enzymes which cleave such hemimethylated target sequences are not to be considered as "restriction endonucleases" excluded from the scope of the second aspect of the invention, but rather are intended to form part of the subject-matter of the invention.

Polynucleotides incorporating one or methylated nucleotides may be prepared using standard techniques for automated DNA synthesis, using appropriately methylated nucleotide precursors. If the template polynucleotide duplex is prepared by solid-phase nucleic acid amplification, then it is convenient to incorporate one or more methylated nucleotides into one of the primers to be used for the amplification reaction.

vi) PCR Stoppers

In another embodiment of the invention the template polynucleotide duplex may be prepared by solid-phase amplification using forward and reverse primers, one of which contains a "PCR stopper". A "PCR stopper" is any moiety (nucleotide or non-nucleotide) which prevents read-through of the polymerase used for amplification, such that it cannot copy beyond that point. The result is that amplified strands derived by extension of the primer containing the PCR stopper will contain a 5' overhanging portion. This 5' overhang (other than the PCR stopper itself) may be comprised of naturally occurring deoxyribonucleotides, with predominantly natural backbone linkages, i.e. it may simply be a stretch of single-stranded DNA. The molecule may then be cleaved in the 5' overhanging region with the use of a cleavage reagent (e.g. an enzyme) which is selective for cleavage of single-stranded DNA but not double stranded DNA, for example mung bean nuclease.

The PCR stopper may be essentially any moiety which prevents read-through of the polymerase to be used for the amplification reaction. Suitable PCR stoppers include, but are not limited to, hexaethylene glycol (HEG), abasic sites, and any non-natural or modified nucleotide which prevents read-through of the polymerase, including DNA analogues such as peptide nucleic acid (PNA).

Stable abasic sites can be introduced during chemical oligonucleotide synthesis using appropriate spacer units containing the stable abasic site. By way of example, abasic furan (5'-O-Dimethoxytrityl-1',2'-Dideoxyribose-3'-[(2-cyanoethyl)-(N,N-diisopropyl)]-phosphoramidite) spacers commercially available from Glen Research, Sterling, Va., USA, can be incorporated during chemical oligonucleotide synthesis in order to introduce an abasic site. Such a site can thus readily be introduced into an oligonucleotide primer to be used in solid-phase amplification. If an abasic site is incorporated into either forward or reverse amplification primer the resulting amplification product will have a 5' overhang on one strand which will include the abasic site (in single-stranded form). The single-stranded abasic site may then be cleaved by the action of a suitable chemical agent (e.g. exposure to alkali) or an enzyme (e.g. AP-endonuclease VI, Shida et al. Nucleic Acids Research, 1996, Vol. 24, 4572-4576).

vii) Cleavage of Peptide Linker

A cleavage site can also be introduced into one strand of a template polynucleotide duplex by preparing a conjugate structure in which a peptide molecule is linked to one strand of the duplex (or the amplification primer from which this strand is derived if prepared by solid-phase amplification). The peptide molecule can subsequently be cleaved by a peptidase enzyme of the appropriate specificity, or any other suitable means of non-enzymatic chemical or photochemical cleavage. Typically, the conjugate between peptide and nucleic acid will be formed by covalently linking a peptide to one strand only of the template polynucleotide duplex, with the peptide portion being conjugated to the 5' end of this strand, adjacent to the point of attachment to the solid surface. If the template polynucleotide duplex is prepared by solid-phase amplification, the peptide conjugate may be incorporated at the 5' end of one of the amplification primers. Obviously the peptide component of this primer will not be copied during PCR amplification, hence the "bridged" amplification product will include a cleavable 5' peptide "overhang" on one strand.

Conjugates between peptides and nucleic acids wherein the peptide is conjugated to the 5' end of the nucleic acid can be prepared using techniques generally known in the art. In one such technique the peptide and nucleic acid components of the desired amino acid and nucleotide sequence can be synthesised separately, e.g. by standard automated chemical synthesis techniques, and then conjugated in aqueous/organic solution. By way of example, the OPeC™ system commercially available from Glen Research is based on the "native ligation" of an N-terminal thioester-functionalized peptide to a 5'-cysteinyl oligonucleotide. Pentafluorophenyl S-benzylthiosuccinate is used in the final coupling step in standard Fmoc-based solid-phase peptide assembly. Deprotection with trifluoroacetic acid generates, in solution, peptides substituted with an N-terminal S-benzylthiosuccinyl group. O-trans-4-(N-a-Fmoc-S-tert-butylsulfenyl-1-cysteinyl)aminocyclohexyl O-2-cyanoethyl-N,N-diisopropylphosphoramidite is used in the final coupling step in standard phosphoramidite solid-phase oligonucleotide assembly. Deprotection with aqueous ammonia solution generates in solution 5'-S-tert-butylsulfenyl-L-cysteinyl functionalized oligonucleotides. The thiobenzyl terminus of the Modified Peptide is converted to the thiophenyl analogue by the use of thiophenol, whilst the Modified Oligonucleotide is reduced using tris(carboxyethyl)phosphine. Coupling of these two intermediates, followed by the "native ligation" step, leads to formation of the Oligonucleotide-Peptide Conjugate.

The conjugate strand containing peptide and nucleic acid can be covalently attached to a solid support using any suitable covalent linkage technique known in the art which is compatible with the chosen surface. If the peptide/nucleic acid conjugate structure is an amplification primer to be used for solid-phase PCR amplification, attachment to the solid support must leave the 3' end of the nucleic acid component free.

The peptide component can be designed to be cleavable by any chosen peptidase enzyme, of which many are known in the art. The nature of the peptidase is not particularly limited, it is necessary only for the peptidase to cleave somewhere in the peptide component. Similarly, the length and amino acid sequence of the peptide component is not particularly limited except by the need to be "cleavable" by the chosen peptidase.

The length and precise sequence of the nucleic acid component is also not particularly limited, it may be of any desired sequence. If the nucleic acid component is to function as a primer in solid-phase PCR, then its length and nucleotide sequence will be selected to enable annealing to the template to be amplified.

viii) Enzymatic Digestion with Restriction Endonuclease/Nicking Endonuclease

Cleavage of double-stranded polynucleotides with restriction endonuclease is a technique in routine use in the art of molecular biology. Nicking endonucleases are enzymes that selectively cleave or "nick" one strand of a polynucleotide duplex and are also well known in the art of molecular biology. The invention is not limited with respect to the nature of the enzyme. Essentially any restriction or nicking endonuclease may be used, provided that a suitable recognition sequence can be included at cleavage site X or cleavage site Y.

As aforesaid, it is essential that cleavage sites X and Y are different. This can be achieved by using a combination of any two of the above-identified means of cleavage, i.e. any combination of two from: enzymatic cleavage, chemical cleavage or photochemical cleavage, etc. In one preferred embodiment a combination of enzymatic cleavage at one site and non-enzymatic cleavage at the other site may be used. If such a combination is used then most preferably cleavage at site X will be enzymatic (e.g. cleavage with restriction enzyme) and cleavage at site Y will be non-enzymatic (preferably a chemical cleavage). It is also possible to use two enzymatic cleavage reactions with restriction endonuclease or nicking endonuclease in combination, provided that the cleavage reactions are different (e.g. two different restriction enzymes which recognise different sites) and that there is no cross-reactivity between sites X and Y.

The method of the invention will now be described in further detail with reference to the accompanying FIG. 1.

FIG. 1(a) illustrates the starting templates for a sequencing reaction according to the invention. The embodiment illustrated uses a mixture of first 1 and second 2 template polynucleotide duplexes immobilised on the surface of a solid support 3. Both strands of each polynucleotide duplex are attached to the solid support at or near the 5' end. The template "duplexes" may in fact be partially single-stranded at one or both 5' ends. Any suitable solid support and any suitable attachment means known in the art may be used, of which several are described by way of example below. Linkage to the solid support will preferably be via covalent attachment.

The polynucleotide duplexes will typically be formed from two complementary polynucleotide strands comprised of deoxyribonucleotides joined by phosphodiester bonds, but may additionally include one or more ribonucleotides and/or non-nucleotide chemical moieties and/or non-naturally occurring nucleotides and/or non-naturally occurring backbone linkages. In particular, the double-stranded nucleic acid may include non-nucleotide chemical moieties, e.g. linkers or spacers, at the 5' end of one or both strands. By way of non-limiting example, the double-stranded nucleic acid may include methylated nucleotides, uracil bases, phosphorothioate groups, ribonucleotides, diol linkages, disulphide linkages, peptides etc. Such non-DNA or non-natural modifications may be included in order to permit cleavage, or to confer some other desirable property, for example to enable covalent attachment to a solid support, or to act as spacers to position a site of cleavage an optimal distance from the solid support.

The first and second template duplexes each comprise a double-stranded target polynucleotide that it is desired to sequence. The template duplexes may also include non-target sequences at both the 5' and 3' ends, flanking the target polynucleotide. If the template duplexes are formed by solid-phase amplification, these non-target sequences will generally be derived from the primers used for solid-phase amplification.

In FIG. 1(a) there is shown, by way of simplification, only a single first duplex 1 and a single second duplex 2 immobilised on a solid support. Although not clearly shown, the first and second duplexes form part of a single cluster or colony comprised of many such first and second duplexes, and the cluster or colony will itself typically form part of an array of many such clusters or colonies. The terms "cluster" and "colony" are used interchangeably throughout and refer to a discrete site on a solid support comprised of a plurality of identical immobilised nucleic acid strands and a plurality of identical immobilised complementary nucleic acid strands. The term "clustered array" refers to an array of such clusters or colonies. In this context the term "array" is not to be understood as requiring an ordered arrangement of clusters. Clustered arrays are generally formed by solid-phase PCR amplification.

A key feature of the invention is that the first and second template duplexes can occur in the same cluster or colony on a clustered array. On such an array the first and second duplexes within each colony will comprise the same double-stranded target polynucleotide and will be derived from amplification of a single target polynucleotide molecule, whereas different colonies may be formed of duplexes comprising different double-stranded target polynucleotides (meaning different to the target polynucleotides present in other colonies), the different colonies being derived from amplification of different single target polynucleotides. In a preferred embodiment at least 90%, more preferably at least 95% of the colonies on a given clustered array will be formed from template duplexes comprising different double-stranded target polynucleotides, although within each individual colony on the array all template duplexes will comprise the same double-stranded target polynucleotide.

Each template duplex comprises a first template strand 4 and a second template strand 5. The first template strand 4 of both the first and second template duplexes comprise a cleavage site Y. Site Y is preferably positioned proximal (or adjacent) to the site of attachment of first template strand 4 to the solid support, such that cleavage at site Y results in removal of a substantial portion of the first template strand leaving behind a large single-stranded region on the complementary strand for the subsequent sequencing reaction.

The second template strand 5 of the first template duplex 1, but not the second template duplex 2, comprises a cleavage site X. Site X is preferably positioned proximal (or adjacent) to the site of attachment of second template strand 5 to the solid support, such that cleavage at site X results in removal of a substantial portion of the first template strand leaving behind a large single-stranded region on the complementary strand for the subsequent sequencing reaction.

If either cleavage site X or cleavage site Y is a site for cleavage by a restriction enzyme, the recognition site (sequence) for the enzyme may be present in a region of the template duplex that is double-stranded when the first and second strands of the template duplex are annealed. The restriction enzyme may cleave both strands of the template duplex or only one strand. For cleavage of both strands, essentially any type of restriction enzyme known in the art may be used. Suitable recognition sites can be included in the template duplexes according to standard molecular biology techniques. By way of example, if the template duplexes are generated by solid-phase amplification then suitable restriction sites may be included in the amplification primers. Examples of enzymes which recognise a double-stranded target sequence but cleave only one strand are the nicking endonucleases, of which many are known in the art. Again, recognition sites for such nicking enzymes may be engineering in the template duplexes using standard techniques.

When using an enzyme which cleaves both strands of an annealed template duplex it is convenient for the cleavage site to be positioned close to the 5' end of the strand it is intended to remove from the solid support via the cleavage reaction, and close to the 3' end of the complementary strand, such that only a small fragment at the 3' end of the complementary strand is removed by the cleavage reaction, but this is not essential.

If either cleavage site X or cleavage site Y is a site for non-enzymatic cleavage, e.g. chemical or photochemical cleavage, then it may be positioned in a region of the template "duplex" that is single-stranded when the first and second strands of the template duplex are annealed, depending on the nature of the cleavage reaction. As outlined above, the template duplexes may in fact be partially single-stranded at one or both 5' ends, proximal to the site of linkage to the solid support. It is within the scope of the invention for cleavage site X and/or cleavage site Y to be positioned within such a single-stranded region, which may be comprised of non-natural nucleotides and/or non-nucleotide chemical moieties etc. as described above.

Following provision of the templates shown in FIG. 1(a) (methods for preparation of such templates are described in further detail below), the second template strand 5 of the first template duplex is cleaved at site X. The resulting products are then denatured to remove the cleaved portion of the second template strand. A first sequencing primer P1 is then hybridised to the first template strand 4 of the first template duplex 1 and a sequencing reaction proceeds via successive incorporation of nucleotides to the first sequencing primer, resulting in determination of the sequence of a first region 6 of the target polynucleotide, this region being in the first template strand.

Hybridisation of sequencing primer P1 to the first template strand is achieved by contacting the primer and template strand under conditions which promote annealing of primer to template. Such conditions will generally be well known to those skilled in the art of molecular biology. Under such conditions annealing of the first and second template strands of the second template duplex is favoured, particularly if the two strands are immobilised in close proximity, such as will be the case if the templates are formed by solid-phase amplification. Hence, the second template duplex structure will re-form under the conditions used for hybridisation of the first sequencing primer to the first template strand.

Duplex formation by annealing of the first and second strands of the second template duplex is favoured over annealing of the first sequencing primer (in free solution) to the first template strand of the second template duplex because of the length of the two complementary strands forming the template duplex and the proximity of the strands on the solid support. However, due to removal of the second template strands 5 of the first duplexes 1 in the first cleavage step there will be an excess of first template strands remaining on the support. Hence, there will be sufficient first template strands available for hybridisation to the first sequencing primer, even after re-formation of the second template duplexes. Thus, the inclusion of a cleavage step to remove a portion of the second template strands prior to hybridisation of the first primer ensures that there are excess first template strands available for hybridisation to the first sequencing primer, even though this hybridisation event is unfavourable compared to re-formation of a template duplex.

When the first sequencing reaction is complete the first template strands 4 of both the first and second duplexes are cleaved at site Y. The resulting products are denatured to remove the cleaved portions of the first template strands. A second sequencing primer P2 is then hybridised to the second template strand 5 of the second template duplex 2 and a sequencing reaction proceeds via successive addition of nucleotides to the second sequencing primer, resulting in determination of the sequence of a second region 7 of the target polynucleotide, this region being in the second template strand.

The sequencing primers P1 and P2 may correspond to adaptor sequences (or a portion thereof) added to the 5' and 3' ends of the target double-stranded molecules to be sequenced (discussed further below), thus enabling common sequencing primers to be used for all target molecules of known or unknown sequence.

Sequencing can be carried out using any suitable "sequencing-by-synthesis" technique, wherein nucleotides are added successively to a free 3' hydroxyl group, typically provided by annealing of a sequencing primer, resulting in synthesis of a polynucleotide chain in the 5' to 3' direction. The nature of the nucleotide added is preferably determined after each addition.

One preferred sequencing method which can be used in the methods of the invention relies on the use of modified nucleotides that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However the detectable label need not be a fluorescent label. Any label can be used which allows the detection of the incorporation of the nucleotide into the DNA sequence.

One method for detecting the fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The methods of the invention are not limited to use of the sequencing method outlined above, but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods.

The target double-stranded polynucleotide to be sequenced using the method of the invention may be any polynucleotide that it is desired to sequence. The target polynucleotide may be of known, unknown or partially known sequence, for example in re-sequencing applications. Using the template preparation method described in detail below it is possible to prepare arrays of templates starting from essentially any double-stranded target polynucleotide of known, unknown or partially known sequence. With the use of arrays it is possible to sequence multiple targets of the same or different sequence in parallel. A particularly preferred application of the method is in the sequencing of fragments of genomic DNA. The method provides particular advantages in the identification of genome rearrangements, since the two regions of sequence obtained for each target molecule using the method will be known to be linked within a certain distance of each other in the genome, depending on the size of the starting target molecule.

Preparation of Templates to be Sequenced

Suitable templates for sequencing using the method of the invention can be prepared using solid-phase nucleic acid (PCR) amplification to produce clustered arrays of nucleic acid colonies. This can be done using procedures analogous to those described in WO 98/44151 and WO 00/18957, the contents of which are incorporated herein in their entirety by reference, except that three primers rather than two are required for amplification of each colony.

For amplification to proceed, a mixture of the three amplification primers is immobilised or "grafted" onto the surface of a suitable solid support.

The three amplification primers are oligonucleotide molecules have the following structures:
First forward primer: A-L-X—S1
Second forward primer: A-L-S1
Reverse primer: A-L-Y—S2

Wherein A represents a moiety which allows attachment to the solid support, L is an optional linker moiety, X is a cleavage site, Y is a cleavage site different to X, and S1 and S2 are polynucleotide sequences which permit amplification of a template nucleic acid molecule comprising the target double-stranded polynucleotide.

The mixture of primers will generally comprise substantially equal amounts of the first and second forward primers and the total amount of the first and second forward primers will typically be substantially equal to the total amount of the reverse primer.

L represents a linker which may be included but is not strictly necessary. The linker may be a carbon-containing chain such as those of formula $(CH_2)_n$ wherein "n" is from 1 to about 1500, for example less than about 1000, preferably less than 100, e.g. from 2-50, particularly 5-25. However, a variety of other linkers may be employed with the only restriction placed on their structures being that the linkers are stable under conditions under which the polynucleotides are intended to be used subsequently, e.g. conditions used in DNA amplification and sequencing.

Linkers which do not consist of only carbon atoms may also be used. Such linkers include polyethylene glycol (PEG) having a general formula of $(CH_2—CH_2—O)_m$, wherein m is from about 1 to 600, preferably less than about 500.

Linkers formed primarily from chains of carbon atoms and from PEG may be modified so as to contain functional groups which interrupt the chains. Examples of such groups include ketones, esters, amines, amides, ethers, thioethers, sulfoxides, sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

As an alternative to the linkers described above, which are primarily based on linear chains of saturated carbon atoms, optionally interrupted with unsaturated carbon atoms or heteroatoms, other linkers may be envisaged which are based on nucleic acids or monosaccharide units (e.g. dextrose). It is also within the scope of this invention to utilise peptides as linkers.

In a further embodiment linker may comprise one or more nucleotides which form part of the amplification primer but which do not participate in any reaction carried out on or with the primer (e.g. a hybridisation or amplification reaction). Such nucleotides may also be referred to herein as "spacer" polynucleotides. Typically from 1 to 20, more preferably from 1 to 15 or from 1 to 10, and more particularly 2, 3, 4, 5, 6, 7, 8, 9 or 10 spacer nucleotides may be included. Most preferably the primer will include 10 spacer nucleotides. It is preferred to use polyT spacers, although other nucleotides and combinations thereof can be used. In one preferred embodiment the primer may include 10T spacer nucleotides.

The one or more spacer nucleotides function to space the portion of the primer required to hybridise to a target and direct amplification, away from the site of attachment to the solid support (i.e. S1 or S2). The inclusion of spacer nucleotides at the 5' end can markedly improve the performance of hybridisation of complementary polynucleotides to region S1 or S2. In the most preferred embodiment the polynucleotide will include 10T spacer nucleotides and a 5' phosphorothioate group for attachment to the solid support (moiety A), although other attachment moieties may be used as discussed below.

Sequences S1 and S2 in the forward and reverse primers are polynucleotide sequences which, in combination, direct amplification of a template by solid-phase PCR. The template to be amplified must itself comprise (when viewed as a single strand) at the 3' end a sequence capable of hybridising to sequence S1 in the forward primers and at the 5' end a sequence the complement of which is capable of hybridising to sequence S2 the reverse primer.

The precise nature of sequences S1 and S2 in the forward and reverse primer oligonucleotides will be dependent on the nature of the template it is intended to amplify. S1 and S2 must be capable of hybridising to cognate sequences on complementary strands of the template to be amplified. The term "hybridisation" encompasses sequence-specific binding between primer and template. Binding of a primer to its cognate sequence in the template should occur under typical conditions used for primer-template annealing in standard PCR. Typically hybridisation conditions are exposure to a temperature in the range of 50-65° C. for a period of about 1 minute in standard PCR reaction buffer, following a denaturation step. Such conditions will be generally well known to those skilled in the art It is not essential for hybridisation that sequences S1 and S2 be exactly complementary to their cognate sequences in the template to be amplified, although this is preferred.

S1 and S2 may be of different or identical sequence and will typically be around 20-30 nucleotides in length. The primers can include natural and non-natural DNA bases, also ribonucleotides or any combination thereof, and may also include non-natural backbone linkages such as disulphides or phosphorothioates.

Cleavage sites X or Y may fall within sequence S1 or S2, or if the linker L is itself a polynucleotide cleavage they may form part of linker region L. In other embodiments the cleavage site may be formed at the junction of sequences L and S1 or L and S2, or at the junction between moiety A and linker L (if present) or between moiety A and sequence S1 or S2 (if L not present).

Moiety A may be any chemical moiety which permits immobilisation of an oligonucleotide primer on a solid support. The surface of the solid support may itself be functionalised to permit attachment of the primers. Any suitable covalent or non-covalent attachment means may be used, of which many are known in the art.

By way of example, biotinylated albumins (BSA) can form a stable attachment of biotin groups by physisorption of the protein onto surfaces. Covalent modification can also be performed using silanes, which have been used to attach molecules to a solid support, usually a glass slide. By way of example, a mixture of tetraethoxysilane and triethoxy-bromoacetamidopropyl-silane (e.g. in a ratio of 1:100) can be used to prepare functionalised glass slides which permit attachment of molecules nucleic acids including a thiophosphate or phosphorothioate functionality. Biotin molecules can be attached to surfaces using appropriately reactive species such as biotin-PEG-succinimidyl ester which reacts with an amino surface. A mixture of amplification primers may then be brought into contact with the functionalised solid support.

In alternative embodiments functionalised polyacrylamide hydrogels may be used to attach primers wherein moiety A is a sulfur-containing nucleophilic groups are used. Examples of appropriate sulfur nucleophile-containing polynucleotides are disclosed in Zhao et al (*Nucleic Acids Research*, 2001, 29 (4), 955-959) and Pirrung et al (*Langmuir*, 2000, 16, 2185-2191) and include, for example, simple thiols, thiophosphates and thiophosphoramidates. Preferred hydrogels are those formed from a mixture of (i) a first comonomer which is acrylamide, methacrylamide, hydroxyethyl methacrylate or N-vinyl pyrrolidinone; and (ii) a second comonomer which is a functionalised acrylamide or acrylate of formula (I):

$$H_2C=C(H)-C(=O)-A-B-C \qquad (I);$$

or a methacrylate or methacrylamide of formula (II):

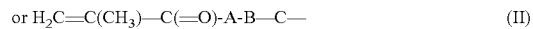
$$\text{or } H_2C=C(CH_3)-C(=O)-A-B-C- \qquad (II)$$

(wherein:

A is NR or O, wherein R is hydrogen or an optionally substituted saturated hydrocarbyl group comprising 1 to 5 carbon atoms;

—B— is an optionally substituted alkylene biradical of formula —$(CH_2)_n$— wherein n is an integer from 1 to 50; and wherein n=2 or more, one or more optionally substituted ethylene biradicals —$CH_2CH_2$— of said alkylene biradical may be independently replaced by ethenylene and ethynylene moieties; and wherein n=1 or more, one or more methylene biradicals —$CH_2$— may be replaced independently with an optionally substituted mono- or polycyclic hydrocarbon biradical comprising from 4 to 50 carbon atoms, or a corresponding heteromonocyclic or heteropolycyclic biradical wherein at least 1 $CH_2$ or $CH_2$ is substituted by an oxygen sulfur or nitrogen atom or an NH group; and C is a group for reaction with a compound to bind the compound covalently to the hydrogel) to form a polymerised product. A particularly preferred hydrogel is formed by co-polymerisation of acrylamide and N-(5-bromoacetamidylpentyl)acrylamide (BRAPA).

The term "solid support", as used herein, refers to the material to which the polynucleotides molecules are attached. Suitable solid supports are available commercially, and will be apparent to the skilled person. The supports can be manufactured from materials such as glass, ceramics, silica and silicon. Supports with a gold surface may also be used. The supports usually comprise a flat (planar) surface, or at least a structure in which the polynucleotides to be interrogated are in approximately the same plane. Alternatively, the solid support can be non-planar, e.g., a microbead. Any suitable size may be used. For example, the supports might be on the order of 1-10 cm in each direction.

For the grafting reaction to proceed a mixture of the three amplification primers is applied to a (suitable functionalised) solid support under conditions which permit reaction between moiety A and the support. The result of the grafting reaction is a substantially even distribution of the three primers over the solid support.

In certain embodiments the template to be amplified may be grafted onto the solid support together with the three amplification primers in a single grafting reaction. This can be achieved by adding template molecules including moiety A at the 5' end to the mixture of primers to form a primer-template mixture. This mixture is then grafted onto the solid support in a single step. Amplification may then proceed using the immobilised template and primers in a reaction analogous to that described in WO 00/18957. The first step in such a reaction will be hybridisation between surface-bound templates and surface-bound amplification primers.

If the mixture of primers only is grafted onto the solid support and the template to be amplified is present in free solution, the amplification reaction may proceed substantially as described in WO 98/44151. Briefly, following attachment of the primers the solid support is contacted with the template to be amplified under conditions which permit hybridisation between the template and the immobilised primers. The template is usually added in free solution under suitable hybridisation conditions, which will be apparent to the skilled reader. Typically hybridisation conditions are, for example, 5×SSC at 40° C., following an initial denaturation step. Solid-phase amplification can then proceed, the first step of the amplification being a primer extension step in which nucleotides are added to the 3' end of the immobilised primer hybridised to the template to produce a fully extended complementary strand. This complementary strand will thus include at its 3' end a sequence which is capable of binding to the second primer molecule immobilised on the solid support. Further rounds of amplification (analogous to a standard PCR reaction) lead to the formation of clusters or colonies of template molecules bound to the solid support.

Sequences S1 and S2 in the amplification primers may be specific for a particular target nucleic acid that it is desired to amplify, but in other embodiments sequences S1 and S2 may be "universal" primer sequences which enable amplification of any target nucleic acid of known or unknown sequence which has been modified to enable amplification with the universal primers.

Suitable templates to be amplified with universal primers may be prepared by modifying target double-stranded polynucleotides by addition of known adaptor sequences to the 5' and 3' ends of the target nucleic acid molecules to be amplified. The target molecules themselves may be any double-stranded molecules it is desired to sequence (e.g. random fragments of human genomic DNA). The adaptor sequences enable amplification of these molecules on a solid support to form clusters using forward and reverse primers having the general structure described above, wherein sequences S1 and S2 are universal primer sequences.

The adaptors are typically short oligonucleotides that may be synthesised by conventional means. The adaptors may be attached to the 5' and 3' ends of target nucleic acid fragments by a variety of means (e.g. subcloning, ligation. etc). More specifically, two different adaptor sequences are attached to a target nucleic acid molecule to be amplified such that one adaptor is attached at one end of the target nucleic acid molecule and another adaptor is attached at the other end of the target nucleic acid molecule. The resultant construct comprising a target nucleic acid sequence flanked by adaptors may be referred to herein as a "template nucleic acid construct".

The target double-stranded polynucleotides may advantageously be size-fractionated prior to modification with the adaptor sequences.

The adaptors contain sequences which permit nucleic acid amplification using the amplification primer molecules immobilised on the solid support. These sequences in the adaptors may be referred to herein as "primer binding sequences". In order to act as a template for nucleic acid amplification, a single strand of the template construct must contain a sequence which is complementary to sequence S1 in the forward amplification primers (such that the forward primer molecule can bind and prime synthesis of a complementary strand) and a sequence which corresponds to sequence S2 in the reverse amplification primer molecules (such that the reverse primer molecule can bind to the complementary strand). The sequences in the adaptors which permit hybridisation to primer molecules will typically be around 20-30 nucleotides in length, although the invention is not limited to sequences of this length.

The precise identity of sequences S1 and S2 in the amplification primers, and hence the cognate sequences in the adaptors, are generally not material to the invention, as long as the primer molecules are able to interact with the amplification sequences in order to direct PCR amplification. The criteria for design of PCR primers are generally well known to those of ordinary skill in the art.

Solid-phase amplification by either the method analogous to that of WO 98/44151 or that of WO 00/18957 will result in production of an array of colonies of "bridged" amplification products having the structures represented in FIG. 1(a). Both strands of the amplification product will be immobilised on the solid support at or near the 5' end, this attachment being derived from the original attachment of the amplification primers. Typically the amplification products within each colony will be derived from amplification of a single target molecule. However, due to the use of three amplification primers each colony will contain a mixture of amplification products in the form of template duplexes, approximately half of which will contain cleavage site X.

The utility of the sequencing method of the invention is not limited to sequencing of templates produced by an amplification reaction, although this is preferred. The method may be applied to sequencing of double-stranded templates immobilised on a support by any other means, provided that the templates include to appropriate combinations of cleavage sites X and Y to enable controlled, independent cleavage of the two complementary template strands.

The invention will be further understood with reference to the following experimental examples:

EXAMPLE

The following are examples of general techniques which may be applied in carrying out the method of the invention.

Acrylamide Coating of Glass Chips

The solid supports used are typically 8-channel glass chips such as those provided by Micronit (Twente, Nederland) or IMT (Neuchâtel, Switzerland). However, the experimental conditions and procedures are readily applicable to other solid supports.

Chips were washed as follows: neat Decon for 30 min, milliQ $H_2O$ for 30 min, NaOH 1N for 15 min, milliQ $H_2O$ for 30 min, HCl 0.1N for 15 min, milliQ $H_2O$ for 30 min.

Polymer Solution Preparation

For 10 ml of 2% polymerisation mix.

10 ml of 2% solution of acrylamide in milliQ $H_2O$

165 µl of a 100 mg/ml N-(5-bromoacetamidylpentyl)acrylamide (BRAPA) solution in DMF (23.5 mg in 235 µl DMF)

11.5 µl of TEMED

100 µl of a 50 mg/ml solution of potassium persulfate in milliQ $H_2O$ (20 mg in 400 µl $H_2O$)

The 10 ml solution of acrylamide was first degassed with argon for 15 min. The solutions of BRAPA, TEMED and potassium persulfate were successively added to the acrylamide solution. The mixture was then quickly vortexed and immediately used. Polymerization was then carried out for 1 h 30 at RT. Afterwards the channels were washed with milliQ H₂O for 30 min. The slide was then dried by flushing argon through the inlets and stored under low pressure in a dessicator.

Synthesis of N-(5-bromoacetamidylpentyl)acrylamide (BRAPA)

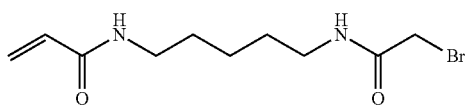 (1)

N-Boc-1,5-diaminopentane toluene sulfonic acid was obtained from Novabiochem. The bromoacetyl chloride and acryloyl chloride were obtained from Fluka. All other reagents were Aldrich products.

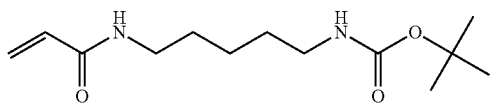 (2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether:ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, $d_6$-DMSO): 1.20-1.22 (m, 2H, CH$_2$), 1.29-1.43 (m, 13H, tBu, 2×CH$_2$), 2.86 (q, 2H, J=6.8 Hz and 12.9 Hz, CH$_2$), 3.07 (q, 2H, J=6.8 Hz and 12.9 Hz, CH$_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for $C_{13}H_{24}N_2O_3$ 256. found 279 (256+Na$^+$).

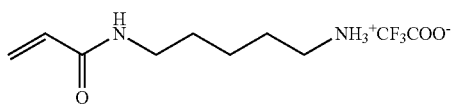 (3)

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, D$_2$O): 1.29-1.40 (m, 2H, CH$_2$), 1.52 (quint., 2H, J=7.1 Hz, CH$_2$), 1.61 (quint., 2H, J=7.7 Hz, CH$_2$), 2.92 (t, 2H, J=7.6 Hz, CH$_2$), 3.21 (t, 2H, J=6.8 Hz, CH$_2$), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for $C_8H_{16}N_2O$ 156. found 179 (156+Na$^+$)

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, $d_6$-DMSO): 1.21-1.30 (m, 2H, CH$_2$), 1.34-1.48 (m, 4H, 2×CH$_2$), 3.02-3.12 (m, 4H, 2×CH$_2$), 3.81 (s, 2H, CH$_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for $C_{10}H_{17}BrN_2O_2$ 276 or 278. found 279 (278+H$^+$), 299 (276+Na$^+$).

Grafting of Primers

The primers are typically 5'-phosphorothioate oligonucleotides incorporating any specific sequences or modifications required for cleavage. Their sequences and suppliers vary according to the experiment they are to be used for.

Grafting is carried out using 80 μl per channel in 10 mM phosphate buffer pH7 for 1 h at RT.

Colony Formation

The PCR template may be hybridised to the grafted primers immediately prior to the PCR reaction. The PCR reaction thus begins with an initial primer extension step rather than template denaturation.

The hybridization procedure begins with a heating step in a stringent buffer (95° C. for 5 minutes in TE) to ensure complete denaturation prior to hybridisation of the PCR template. Hybridization is then carried out in 5×SSC, using template diluted to the desired final concentration. After the hybridization, the chip was washed for 5 minutes with milliQ water to remove salts.

Surface amplification is carried out by thermocycled PCR in an MJ Research thermocycler.

A typical PCR program is as follows:
1—97.5° C. for 0:45
2—X° C. for 1:30
3—73° C. for 1:30
4—Goto 1 [40] times
5—73° C. for 5:00
6—20° C. for 3:00
7—End Since the first step in the amplification reaction is extension of the primers bound to template in the initial hybridisation step the first denaturation and annealing steps of this program are omitted (i.e. the chip is placed on the heating block only when the PCR mix is pumped through the flow cell and the temperature is at 73° C.).

The annealing temperature (X° C., step 2) depends on the primer pair that is used, but is typically in the range of 55-58° C. For other primer-pairs the optimum annealing temperature can be determined by experiment. The number of PCR cycles may be varied if required.

PCR is carried out in a reaction solution comprising 1×PCR reaction buffer (supplied with the enzyme) 1M betain, 1.3% DMSO, 200 µM dNTPs and 0.025 U/µL Taq polymerase.

Linearisation/Cleavage (1) Restriction Enzyme Digestion

The surface equivalent of roughly a solution amount of 1.25 pmoles of DNA is digested at 37° C. for 30 minutes with restriction enzyme (50 Units/mL final concentration) in its supplied buffer from the manufacturer at "1×" final concentration.

(2) Cleavage of Diol Linkages

Diol linkages can be introduced by including a suitable linkage into one of the primers used for solid-phase amplification.

Suitable primers including any desired template-specific sequence can be manufactured by standard automated DNA synthesis techniques using components available from commercial suppliers (e.g. Fidelity Systems Inc., ATD).

A cleavable diol-containing primer would typically have the following structure:

5'-phosphorothioate-arm 26-diol22A-sequence-3'OH

Wherein "sequence" represents a sequence of nucleotides capable of hybridising to the template to be amplified.

The structures of the arm26 and diol22A components (from Fidelity Systems Inc, MD, USA) are as follows:

e.g., by using thiophosphate linkages in one side of the restriction enzyme recognition site, to prevent cutting in that side, but not in the other.

(5) TCEP Cleavage of Disulphide

This procedure may be used when one strand of the template duplex contains a disulfide group, typically positioned between the site of attachment to the solid support (e.g. an amino group necessary for the binding of the polynucleotide to a functionalized silane support) and the first nucleotide. This disulfide bond is cleaved using Tris(2-carboxyethyl)-phosphate hydrochloride (TCEP).

Linearization is carried out at room temperature in a TCEP/Tris solution. Aliquots of pre-weighted TCEP (about 10 mg per aliquot) are stored at 4° C. The powder is dissolved in Tris-HCl 100 mM pH 7.5 to get a final TCEP concentration of 14.3 mg/ml (corresponding to 50 mM). TCEP is sensitive to oxidation.

Templates to be linearised are typically exposed to TCEP/Tris for 30 minutes then washed with 0.1×SSC-0.1% Tween, then with 5×SSC.

Thermal Dehybridisation

Thermal denaturation or de-hybridization of colonies is carried out in stringent buffer (TE). Typically the temperature is ramped 0.5° C./sec to 97.5° C. and held at 97.5° C. for 2 minutes 30 seconds.

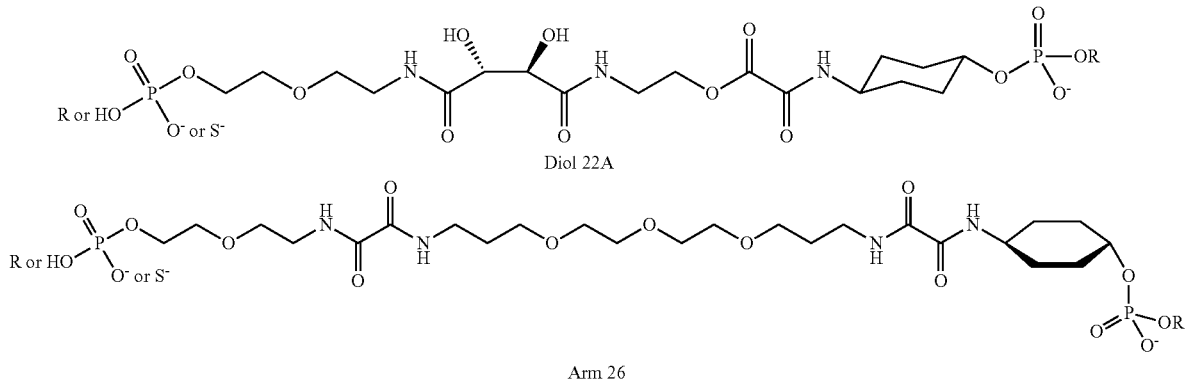

Diol 22A

Arm 26

Products containing such diol linkages can be cleaved by treatment with sodium periodate (e.g. 0.1M sodium periodate in water for 30 min at room temperature).

(3) Cleavage of U-Containing DNA with Uracil DNA Glycosylase.

After an appropriate wash, chips containing DNA can be incubated in 14 parts UDG Buffer (70 mM Hepes-KOH pH 8.0, 1 mM dithiothreitol, 1 mM EDTA), 1 part uracil DNA glycosylase (BRL). After e.g. two hours of incubation at 37° C. the chips are optionally washed with a high pH wash solution and heated to 94° C. for up to 10 min to kill the enzyme.

(4) Nicking Reaction.

The surface equivalent of roughly a solution amount of 1.25 pmoles of DNA is digested at 55° C. for 30 minutes with nicking endonuclease (e.g. N.BstNBI) (50 Units/mL final concentration) in its supplied buffer (e.g. NEBuffer N.BstNBI at "1×" final concentration) from the manufacturer.

It will be appreciated that nicking can also be accomplished by blocking one side of a standard restriction enzyme cleavage site using methods familiar to those skilled in the art, Sequencing (1) Hybridisation of Sequencing Primer The procedure begins with a heating step in a stringent buffer (TE) to ensure complete denaturation of the colonies prior to hybridisation of the primer.

Hybridization of the sequencing primer is typically carried out in 5×SSC, using an oligonucleotide diluted to a final concentration of 500 nM. This solution should be prepared just before use, especially when fluorophore-labelled oligonucleotides are used.

Typical temperature cycling profile is typically as follows:
MJ-Research Thermocycler program set:
(Control method: block)
1—0.5° C./sec to 97.5° C.
2—97.5° C. for 2:30
3—97.5° C. for 0:02
 —0.1° C. per cycle
4—Goto 3 for 574 times
5—40° C. for 15:00
6—End (2) Long Read Sequencing Protocol Sequencing may be carried out using modified nucleotides prepared as described in International patent application WO 2004/018493, and labelled with four different commercially available fluorophores (Molecular Probes Inc.).

A mutant 9° N polymerase enzyme (an exo-variant including the triple mutation L408Y/Y409A/P410V and C223S) may be used for the nucleotide incorporation steps.

Enzyme mix (enzymology buffer above plus 50 μg/ml of the enzyme, and 1 μM each of the four labelled modified nucleotides) is applied to the sequencing templates, typically for 2 min 30 s, and heated to 45° C.

Templates are maintained at 45° C. for 30 min, cooled to 20° C. and washed for 5 min with enzymology buffer, then 5 min with 5×SSC. Templates are then exposed to an imaging buffer of 100 mM Tris pH7.0, 30 mM NaCl, 50 mM sodium ascorbate (freshly dissolved, filtered).

Incorporated nucleotides are detected using suitable fluorescent, imaging apparatus.

The invention claimed is:

1. A method for pairwise sequencing of first and second strands of target polynucleotides, wherein the first and second strands of each target polynucleotide have complementary sequences, the method comprising:
   (a) forming a plurality of nucleic acid colonies by solid phase nucleic acid amplification, wherein each of the nucleic acid colonies comprises multiple copies of a first strand and a complementary second strand formed by amplification of a single originating target polynucleotide;
   (b) forming a single-stranded region in a subset of the first strands in each of the colonies and hybridizing first sequencing primers to the single-stranded region; whereby after hybridizing said sequencing primer, the colonies comprise a plurality of intact duplexes on the solid support, the intact duplexes comprising a portion of the multiple colonies of the first strand and a complementary second strand;
   (c) carrying out a first sequencing reaction by sequential addition of nucleotides to the first sequencing primers to determine sequences from the first strands;
   (d) cleaving the first strands;
   (e) removing at least a portion of the first strands from the colonies, whereby a single-stranded region is formed in second template strands of the intact duplexes;
   (f) hybridizing second sequencing primers to second strands of the colonies;
   (g) carrying out a second sequencing reaction by sequential addition of nucleotides to the second sequencing primers to determine sequences from the second strands, wherein the first sequencing reaction and the second sequencing reaction permit pairwise sequencing of the target polynucleotides.

2. The method of claim 1, wherein the nucleic acid colonies are attached to beads.

3. The method of claim 1, wherein the nucleic acid colonies are attached to a planar surface.

4. The method of claim 1, wherein the nucleotides that are added in the first sequencing reaction and in the second sequencing reaction comprise reversible blocking groups.

5. The method of claim 1, wherein the nucleotides that are added in the first sequencing reaction and in the second sequencing reaction comprise labels.

6. The method of claim 1, wherein the first sequencing reaction and the second sequencing reaction comprise pyrosequencing.

7. The method of claim 1, wherein the first sequencing reaction and the second sequencing reaction comprise sequencing-by-synthesis.

8. The method of claim 1, wherein the cleaving of the first strands comprises enzymatic cleavage.

9. The method of claim 1, wherein the cleaving of the first strands comprises chemical cleavage.

10. The method of claim 1, wherein the cleaving of the first strands comprises photochemical cleavage.

11. The method of claim 1, wherein the cleaving of the first strands comprises cleaving an abasic site.

12. The method of claim 1, wherein the cleaving of the first strands comprises nicking the first strands.

13. The method of claim 1, wherein the sequencing is carried out using a sequencing primer in solution.

14. The method of claim 1, wherein the target polynucleotides comprise known adaptor sequences on the 5' and 3' ends of the first and second strands.

15. The method of claim 1, wherein the first sequencing reaction and the second sequencing reaction permit pairwise sequencing of separate and distinct regions on the complementary strands of each of the target polynucleotides.

16. The method of claim 1, wherein the first sequencing reaction determines sequences of regions of the first strands, wherein the second sequencing reaction determines sequences of regions of the second strands, and wherein the regions of the first strands are not complementary to the regions of the second strands.

17. The method of claim 1, wherein the first sequencing reaction determines sequences of regions of the first strands, wherein the second sequencing reaction determines sequences of regions of the second strands, and wherein the regions of the first strands are complementary to the regions of the second strands.

* * * * *